(12) United States Patent
Nappa et al.

(10) Patent No.: US 8,299,309 B2
(45) Date of Patent: Oct. 30, 2012

(54) SYNTHESIS OF HYDROFLUOROALKANOLS AND HYDROFLUOROALKENES

(75) Inventors: Mario Joseph Nappa, Newark, DE (US); Xuehui Sun, Swedesboro, NJ (US); Lev Moiseevich Yagupolskii, Kiev (UA); Andrey Anatolievich Filatov, Kiev (UA); Vladimir Nikolaevich Boiko, Kiev (UA); Yurii Lvovich Yagupolskii, Kiev (UA)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/270,489

(22) Filed: Oct. 11, 2011

(65) Prior Publication Data

US 2012/0083619 A1 Apr. 5, 2012

Related U.S. Application Data

(62) Division of application No. 12/274,728, filed on Nov. 20, 2008, now Pat. No. 8,058,488.

(60) Provisional application No. 61/104,334, filed on Oct. 10, 2008.

(30) Foreign Application Priority Data

Nov. 21, 2007 (UA) .............................. A200712916

(51) Int. Cl.
*C07C 17/00* (2006.01)

(52) U.S. Cl. ........ 570/171; 570/123; 570/124; 570/134; 570/135; 570/153

(58) Field of Classification Search ........................ None
See application file for complete search history.

(56) References Cited

U.S. PATENT DOCUMENTS

| | | | | |
|---|---|---|---|---|
| 2,992,276 | A * | 7/1961 | Weinmayr | ................ 568/683 |
| 7,026,520 | B1 * | 4/2006 | Mukhopadhyay et al. | ... 570/123 |
| 2007/0112227 | A1 * | 5/2007 | Mukhopadhyay et al. | ... 570/101 |

FOREIGN PATENT DOCUMENTS

| | | |
|---|---|---|
| EP | 0157739 B1 | 12/1987 |
| FR | 1496633 A | 9/1967 |

OTHER PUBLICATIONS

Robert Werner Lang, A Simple Synthesis of 2,2-Dichloro-3,3,3-Trifluoropropanol, Helvetica Chimica Acta, vol. 69 (1986), Fluorine-Containing Organozinc Reagents, pp. 881-886.

O. Paleta, et al, The Chemo-Selective Reduction of Fluorinated Halogenoesters With Sodium Borohydride. Fluorinated Halogenoalkanols and Their (METH)Acrlates, Journal of Fluorine Chemistry, 45 (1989), pp. 331-348, Department of Organic Chemistry, Prague Institute of Chemical Technology, Czech Republic.

Kitazume et al: "A Remarkably Simple Perfluoroalkylation in the Presence of an Electron Mediator", J. Org. Chem., vol. 53, 1988, pp. 2350-2352, XP002508766, Table 1, Scheme 1.

Dolbier, William R., Jr., et al, "Hydrogen Fluoride-Tetrahydrofuran as a Fluorinating Medium. A General Synthesis of 1,1,1,2-Tetrafluoro-2-Alkenes", Synthesis, (10), 956-8 Coden: SYNTBF; ISSN 0039-7881, 1987, XP002508655, p. 956, col. 2, Compounds 1, 2, 2A, 2B.

H. C. Brown: "Thermal Reactions of Perfluorobutyne-2 and Perfluoropropene" J. Org. Chem., vol. 22, 1957, pp. 1256-1257, XP002508767, Compound IV.

International Search Report, PCT/US08/84107, Dated Jan. 26, 2009.

* cited by examiner

*Primary Examiner* — Sudhakar Katakam

(57) ABSTRACT

Described herein is a process for the manufacture of hydrofluoroalkanols of the structure $R_fCFClCHROH$. Also described herein are methods of manufacturing hydrofluoroalkenes of the structure $R_fCF{=}CHR$ from halofluorocarbons of the structure $R_fCFX_2$. In particular, 2,3,3,3,-tetrafluoro-1-propene may be manufactured with this process. Also described are compounds of the formula $R_fCFClCHROC({=}O)R'$.

5 Claims, No Drawings ured as a result of the Montreal Protocol. The solution for most refrigerant producers has been the commercialization of hydrofluorocarbon (HFC) refrigerants. HFC's, however, are now being regulated due to concerns related to global warming.

SYNTHESIS OF HYDROFLUOROALKANOLS AND HYDROFLUOROALKENES

CROSS REFERENCE(S) TO RELATED APPLICATION(S)

This application is a divisional of pending U.S. patent application Ser. No. 12/274,728, filed Nov. 20, 2008, which claims the priority benefit of Ukrainian Patent Application No. A200712916, filed Nov. 21, 2007 and U.S. Provisional Patent Application 61/104,334, filed Oct. 10, 2008.

BACKGROUND

1. Field of the Disclosure

This disclosure relates in general to a process for the production of hydrofluoroalkanols, and a process for the production of hydrofluoroalkenes, and in particular a process for the production of 2,3,3,3-tetrafluoro-1-propene, from hydrofluoroalkanols and hydrofluoroalkanol esters.

2. Description of the Related Art

The refrigeration industry has been working for the past few decades to find replacement refrigerants for the ozone depleting chlorofluorocarbons (CFC's) and hydrochlorofluorocarbons (HCFC's) being phased out as a result of the Montreal Protocol. The solution for most refrigerant producers has been the commercialization of hydrofluorocarbon (HFC) refrigerants. HFC's, however, are now being regulated due to concerns related to global warming.

There is always a need for new and better processes for the preparation of halocarbons that may be useful as refrigerants or in other applications such as foam expansion agents, aerosol propellants, fire suppression or extinguishing agents, solvents, and sterilants to name a few.

SUMMARY OF THE INVENTION

The present invention provides for the manufacture of hydrofluoroalkanols and hydrofluoroalkenes. Described herein is a process for the manufacture of hydrofluoroalkanols of the structure $R_fCFXCHROH$, comprising reacting a halofluorocarbon of the structure $R_fCFX_2$, wherein each X is independently selected from Cl, Br, and I, with an aldehyde and a reactive metal in a reaction solvent to generate a reaction product comprising a metal hydrofluoroalkoxide, neutralizing said the metal hydrofluoroalkoxide to produce a hydrofluoroalkanol, and, optionally, recovering the hydrofluoroalkanol.

Also described herein are methods of manufacturing hydrofluoroalkenes from halofluorocarbons of the structure $R_fCFX_2$, wherein each X is independently selected from Cl, Br, and I, comprising reacting halofluorocarbons of the structure $R_fCFX_2$, wherein each X is independently selected from Cl, Br, and I with an aldehyde and a reactive metal in a reaction solvent to generate a reaction product comprising a metal hydrofluoroalkoxide, and reductively dehydroxyhalogenating the metal hydrofluoroalkoxide to produce a hydrofluoroalkene, and, optionally, recovering the hydrofluoroalkene. In one embodiment, the reductive dehydroxyhalogenation comprises reacting the metal hydrofluoroalkoxide with a carboxylic acid anhydride and a reactive metal to form the hydrofluoroalkene. In another embodiment, the reductive dehydroxyhalogenation comprises neutralizing the metal hydrofluoroalkoxide to produce a hydrofluoroalkanol, mixing a dehydrating agent with said hydrofluoroalkanol thereby forming a gaseous mixture, and contacting a catalyst with said gaseous mixture, thereby forming the hydrofluoroalkene.

Also described herein are methods of manufacturing 2,3,3,3-tetrafluoro-1-propene. The methods comprise the steps of manufacturing hydrofluoroalkenes as described above, wherein $R_f$ is $CF_3$.

Also disclosed herein are novel hydrofluoroalkanol esters of the formula $R_fCFXCH_2OC(=O)R$, where $R_f$ is a perfluoroalkyl group having from one to four carbon atoms, R is $CH_3$, $CH_3CH_2$, $CH_3CH_2CH_2$, $(CH_3)_2CH$ or H, X is selected from Cl, Br, and I, and R' is selected from the group consisting of —$CH_3$, —$C_2H_5$, —$CH_2CH_2CH_3$, $CH_2CH_2CO_2H$, $CH_2CH_2CH_2CO_2H$, $CH_2CH_2CH_2CH_2CO_2H$ and H, and novel hydrofluorocarbons of the formula cyclo-(—CF($R_f$)CHRCF($R_f$)CHR—).

Also disclosed is a method for the manufacture of hydrofluoroalkenes of the structure $R_fCF=CHR$, comprising reacting a hydrofluoroalkanol of structure $R_fCFXCHROH$ or a hydrofluoroalkoxide of structure $R_fCFXCHROMX$, wherein M is a reactive metal in the +2 oxidation state and wherein X is selected from Cl, Br, and I, with a carboxylic acid anhydride and a reactive metal in a reaction solvent to form a hydrofluoroalkene, and isolating the hydrofluoroalkene.

Also disclosed herein is a compound having the formula $R_fCFXCHRO—Zn—X$, where $R_f$ is a perfluoroalkyl group having from one to four carbon atoms, X is selected from Cl, Br, and I, and R is $CH_3$, $CH_3CH_2$, $CH_3CH_2CH_2$, $(CH_3)_2CH$ or H.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description and from the claims.

DETAILED DESCRIPTION

Before addressing details of embodiments described below, some terms are defined or clarified.

As used herein, formaldehyde refers to the compound having the structure $H_2C=O$, which is also known to occur in the form of a cyclic trimer 1,3,5-trioxane, and also as paraformaldehyde or polyoxymethylene.

As used herein, reactive metal refers to reactive metals such as magnesium turnings, activated zinc powder, aluminum, and a powder of any of the following metals: magnesium, calcium, titanium, iron, cobalt, nickel, copper, zinc and indium, and also zinc(II) salts. Magnesium turnings are pieces of magnesium which are cut to produce small pieces with higher surface areas and generally low amounts of surface oxides (which reduce reactivity). The reactive metal powders of magnesium, calcium, titanium, iron, cobalt, nickel, copper, zinc and indium are Rieke metals, which are prepared by a specific procedure which produces high surface area metal powders which are very reactive in reactions such as those of the present invention. Without wishing to be bound by any particular theory, Rieke metals are thought to be highly reactive because they have high surface areas and lack passivating surface oxides.

As used herein, a dehydrating agent is a gas or gaseous mixture containing at least one gas selected from the group consisting of: methane, ethane, propane, butane, natural gas, alcohols, aldehydes, and carbon monoxide. As used herein, natural gas refers to a gaseous mixture having methane as the major component, but also comprising quantities of ethane, butane, propane, carbon dioxide, nitrogen.

As used herein dehydroxyhalogenating refers to removing a hydroxyl group and a halogen atom, chosen from Cl, Br and I, from adjacent carbon atoms of a hydrofluoroalkanol to form a hydrofluoroalkene.

In one embodiment, hydrofluoroalkanols of the formula $R_fCFXCHROH$, such as 1,1,1,2-tetrafluoro-2-chloropropanol, an intermediate that may be converted into 2,3,3,3-tetrafluoro-1-propene (HFC-1234yf), are prepared. In one embodiment, R is selected from the group consisting of $CH_3$, $CH_3CH_2$, $CH_3CH_2CH_2$, $(CH_3)_2CH$ or H. In one embodiment, $R_f$ is a perfluoroalkyl group having from one to four carbon atoms. In another embodiment, $R_f$ is selected from the group consisting of perfluoromethyl, perfluoroethyl, perfluoro-n-propyl, perfluoro-i-propyl, perfluoro-n-butyl and perfluoro-i-butyl, respectively, i.e., $CF_3$—, $CF_3CF_2$—, $CF_3CF_2CF_2$—, $(CF_3)_2CF$—, $CF_3CF_2CF_2CF_2$— and $CF_3CF(CF_3)CF_2$—, respectively. In one embodiment, $R_f$ is $CF_3$ and R is H. In one embodiment X is selected from Cl, Br, and I. In another embodiment, X is Cl.

In one embodiment, halofluorocarbons of the formula $R_fCFX_2$, wherein each X is independently selected from Cl, Br, and I, are reacted with an aldehyde, and a reactive metal in a reaction solvent to generate a metal hydrofluoroalkoxide. In one embodiment the metal hydrofluoroalkoxide is neutralized to provide a hydrofluoroalkanol, which can be isolated. In some embodiments, the neutralization comprises dilution with an organic solvent, and reaction with a dilute aqueous solution of an acid, including without limitation dilute aqueous hydrochloric acid or dilute aqueous sulfuric acid. Upon separation of the organic solvent phase from the aqueous phase, in some embodiments, the organic solvent phase is washed further with an aqueous salt solution. The organic solvent phase is then dried and the solvent removed by evaporation or distillation to provide the hydrofluoroalkanol product. In other embodiments, the metal hydrofluoroalkoxide may be used in further reactions as described later to produce a hydrofluoroalkene without neutralization. In one embodiment, the halofluorocarbon is 1,1,dichlorotetrafluoroethane and the hydrofluoroalkanol is 2-chloro-2,3,3,3-tetrafluoro-1-propanol.

Halofluorocarbons of the formula $R_fCFX_2$, wherein each X is independently selected from Cl, Br, and I may be prepared by halogenation of the corresponding hydrofluorocarbons $R_fCFH_2$. For example, in one embodiment where $R_f$ is $CF_3$ and X is Cl, 1,1,1,2-tetrafluoroethane (HFC-134a) is chlorinated to prepare 1,1,1,2-tetrafluoro-2,2-dichloroethane (CFC-114a).

In some embodiments, in addition to the reactive metal, a zinc salt is added to the mixture comprising the reaction of the halofluorocarbon. Suitable zinc salts include zinc acetate, zinc bromide, zinc chloride, zinc citrate, zinc sulfate and mixtures thereof. In one embodiment, the zinc salt is zinc acetate. In one embodiment, the amount of zinc salt added is from 0.1 to 1.0 mole per mole of halofluorocarbon. In another embodiment, the amount of zinc salt added is from 0.25 to 0.7 mole per mole of halofluorocarbon. In another embodiment, the amount of zinc salt added is from 0.5 to 0.6 mole per mole of halofluorocarbon.

In one embodiment, the aldehyde is selected from the group consisting of formaldehyde, acetaldehyde, propionaldehyde, butyraldehyde and isobutyraldehyde. In one embodiment, the mole ratio of reactive metal to halofluorocarbon is about 1:1. In another embodiment, the mole ratio of reactive metal to halofluorocarbon is about 2:1. In yet another embodiment, the mole ratio of reactive metal to halofluorocarbon is about 2.5:1. In one embodiment, the mole ratio of aldehyde to halofluorocarbon is about 1:1. In another embodiment, the mole ratio of aldehyde to halofluorocarbon is about 2:1. In yet another embodiment, the mole ratio of aldehyde to halofluorocarbon is about 3:1.

In some embodiments where paraformaldehyde is used as the aldehyde, a quaternary ammonium salt is added to the reaction. In one embodiment, the quaternary ammonium salt is a bis-alkyldimethyl ammonium acetate. Without wishing to be bound by any particular theory, such quaternary ammonium salts are believed to promote the decomposition of paraformaldehyde to formaldehyde. In some embodiments the amount of quaternary ammonium salt added is from about 1% to about 20% by weight of the amount of paraformaldehyde. In other embodiments, the amount of quaternary ammonium salt added is from about 5% to about 10% by weight of the amount of paraformaldehyde.

The reaction of the halofluorocarbon with an aldehyde and reactive metal is conducted in a reaction solvent. In one embodiment, the reaction solvent is selected from the group consisting of alkyl, dialkyl, and trialkyl linear or cylic amines, N-methylpyrrolidine, N-methylpiperidine, sulfoxides, ethers, pyridine or alkyl-substituted pyridines, pyrazine or pyrimidine, alkyl and aromatic nitriles, hexamethylphosphoramide, alcohols, esters, and mixtures thereof. In one embodiment, an alcohol solvent is methanol. In one embodiment, an ester solvent is methyl formate. In one embodiment, a sulfoxide solvent is dimethylsulfoxide. In one embodiment, an alkyl nitrile solvent is acetonitrile. In one embodiment, an aromatic nitrile solvent is benzonitrile. In another embodiment, the reaction solvent is selected from the group consisting of trialkylamines, N-methylpyrrolidine, N-methylpiperidine, pyridine, alkyl-substituted pyridines, dimethylformamide, pyrazine or pyrimidine, and mixtures thereof. In another embodiment, the reaction solvent is selected from the group consisting of dimethylformamide, tetrahydrofuran, pyridine, dimethylacetamide, 1,4-dioxane, N-methylpyrrolidone, diethyl ether, and mixtures thereof. In yet another embodiment, the reaction solvent is pyridine or alkyl-substituted pyridines, or mixtures thereof. In yet another embodiment, the reaction solvent is a mixture of pyridine or alkyl-substituted pyridines, and dimethylformamide.

In one embodiment, the amount of water present in the reaction of the halofluorocarbon with an aldehyde and reactive metal is less than 1000 ppm. In another embodiment, the amount of water present in the reaction of the halofluorocarbon with an aldehyde and reactive metal is about 500 ppm. In yet another embodiment, the amount of water present in the reaction of the halofluorocarbon with an aldehyde and reactive metal is from about 100 to about 300 ppm.

In one embodiment, the reaction of the halofluorocarbon with an aldehyde and reactive metal is performed at a temperature of from about 30° C. to about 100° C. In another embodiment, the reaction of the halofluorocarbon with an aldehyde and reactive metal is performed at a temperature of from about 50° C. to about 80° C. In one embodiment, the reaction is conducted for from about 3 to about 10 hours. In another embodiment, the reaction of the halofluorocarbon with an aldehyde and reactive metal is conducted for from about 4 to about 8 hours. In yet another embodiment, the reaction of the halofluorocarbon with an aldehyde and reactive metal is conducted for from about 4 to about 6 hours.

In one embodiment, the aldehyde is pre-treated with the reaction solvent for a period of time before the reaction. In one embodiment paraformaldehyde is pre-treated in pyridine for four hours at 60° C. prior to reaction with halofluorocarbon and reactive metal. In one embodiment, the pre-treatment occurs for two hours. In another embodiment, the pre-treatment occurs for six hours. In still other embodiments, there is no pre-treatment, and the reaction is commenced upon charging all of the reactants and reaction solvent to the reaction vessel sequentially.

In one embodiment, the reaction of the halofluorocarbon with an aldehyde and reactive metal is performed in a closed vessel or other reactor. In one embodiment the reaction of the halofluorocarbon with an aldehyde and reactive metal is performed under autogenous pressure. In another embodiment, the reaction of the halofluorocarbon with an aldehyde and reactive metal is performed in an open vessel or reactor, equipped with a suitable condenser to prevent escape of unreacted halofluorocarbon.

According to another aspect of the present invention, there is provided a process for the manufacture of hydrofluoroalkenes of the structure $R_fCF=CHR$. This process comprises reacting a halofluorocarbon of the structure $R_fCFX_2$ with an aldehyde and a reactive metal to generate a metal hydrofluoroalkoxide, reductively dehydroxyhalogenating said reaction product in a second step to produce a hydrofluoroalkene, and then isolating the hydrofluoroalkene.

In one embodiment, $R_f$ is a perfluoroalkyl group having from one to four carbon atoms. In a particular embodiment, $R_f$ is $CF_3$ and R is H.

In one embodiment, the process for producing a hydrofluoroalkene comprises neutralizing the reaction product to produce a hydrofluoroalkanol; mixing a dehydrating agent with the hydrofluoroalkanol, thereby forming a gaseous mixture; and contacting a catalyst with the gaseous mixture, thereby forming the hydrofluoroalkene.

In one embodiment, the reaction product of a chlorofluoroalkane, an aldehyde and a reactive metal is neutralized by diluting the reaction product mixture with a mixture of a solvent, ice, and an aqueous solution of an acid. In one embodiment, the solvent can be any commonly used organic solvent, such as diethyl ether. In one embodiment, the aqueous solution of an acid is an aqueous solution of a common mineral acid, such as hydrochloric acid. After stirring the resulting mixture for a period of time, the layer comprising the organic solvent is separated. In one embodiment, the organic solvent layer can be subsequently washed with a dilute aqueous solution of an acid, followed by a brine solution. The organic layer is then dried. In some embodiments, the drying is accomplished by stirring the organic layer over and anhydrous salt, such as anhydrous magnesium sulfate or anhydrous sodium sulfate. In some embodiments, the organic solvent can then be evaporated to afford the hydrofluoroalkanol.

In this embodiment, the hydrofluoroalkanol is at least one selected from the group consisting of: fluoroalkanols having the general formula $R_f'CH_2OH$ wherein $R_f'$ is selected from the group consisting of: $CF_3CFCl—$, $CF_3CF_2CFCl—$, $CF_3CF_2CF_2CFCl—$ and $CF_3CF_2CF_2CF_2CFCl—$. In one embodiment, the hydrofluoroalkanol is 2,3,3,3-tetrafluoro-2-chloro-1-propanol.

In one embodiment, the catalyst is at least one transition metal. The metal is selected from the group consisting of: nickel (Ni), palladium (Pd), and platinum (Pt). In one embodiment, the catalyst is a supported catalyst which comprises a transition metal and a support material. The support material is at least one selected from the group consisting of activated carbon and λ-alumina.

The dehydrating agent is at least one gas selected from the group consisting of: methane, ethane, propane, butane, natural gas, alcohols, aldehydes, and carbon monoxide.

The mixing step takes place at a temperature in the range between about 65-80° C.

The process further comprises preheating the gaseous mixture prior to the contacting step. The preheating takes place at a temperature in the range between about 250 to about 450° C.

The contacting step preferably takes place at a temperature in the range between about 400 to about 700° C. The contacting step also preferably takes place for between about 20 to about 25 seconds.

The process further comprises the step of neutralizing any residual HF contained in the hydrofluoroalkene product, wherein the HF is neutralized by passing the hydrofluoroalkene product through a KOH solution.

The hydrofluoroalkene product comprises at least one hydrofluoroalkene selected from the group consisting of: 2,3,3,3-tetrafluoro-1-propene or any hydrofluoroalkene selected from the group consisting of compounds represented by the formula: $R_fCF=CH_2$ wherein $R_f$ is selected from the group consisting of: $CF_3$, $CF_3CF_2$, $CF_3CF_2CF_2$, $(CF_3)_2CF—$, $CF_3CF_2CF_2CF_2—$ and $CF_3CF(CF_3)CF_2—$.

The gaseous mixture may further comprise at least one diluent inert gas selected from the group consisting of: nitrogen, helium, and argon.

The conversion of the hydrofluoroalkanol to hydrofluoroalkene is in the range between about 50 to about 100%. The selectivity of hydrofluoroalkanol to hydrofluoroalkene is in the range between about 29 to about 100%.

The pressure during the contacting step is in the range between about 1 to about 100 psig.

Further in accordance with the present invention, there is provided a process for the manufacture of hydrofluoroalkenes of the structure $R_fCF=CHR$, comprising reacting a hydrofluoroalkanol of structure $R_fCFXCHROH$ or a hydrofluoroalkoxide of structure $R_fCFXCHROMX$, wherein M is a reactive metal in the +2 oxidation state, with a carboxylic acid anhydride and a reactive metal in a reaction solvent to form a hydrofluoroalkene, and isolating the hydrofluoroalkene.

In another embodiment, the reductive dehydroxyhalogenation comprises reacting the metal hydrofluoroalkoxide with a carboxylic acid anhydride and a reactive metal. In this embodiment, hydrofluoroalkenes of the structure $R_fCF=CHR$ are manufactured by reacting a hydrofluoroalkanol of structure $R_fCFXCHROH$ or a hydrofluoroalkoxide of structure $R_fCFXCHROMX$, wherein M is a reactive metal in the +2 oxidation state, with a carboxylic acid anhydride and a reactive metal in a reaction solvent to form a hydrofluoroalkene, and optionally, isolating the hydrofluoroalkene. In this embodiment, the hydrofluoroalkanol of structure $R_fCFXCHROH$ or a hydrofluoroalkoxide of structure $R_fCFXCHROMX$, wherein M is a reactive metal in the +2 oxidation state, react first with the carboxylic acid anhydride to form an ester as described below. This ester then reacts with the reactive metal to form a hydrofluoroalkene. In this process $R_f$ is selected from the group consisting of perfluoromethyl, perfluoroethyl, perfluoro-n-propyl, perfluoro-i-propyl, perfluoro-n-butyl and perfluoro-i-butyl, X is selected from Cl, Br, and I, and R is selected from the group consisting of H, $CH_3$, $C_2H_5$, n-$C_3H_7$, and i-$C_3H_7$, and in particular $R_f$ is $CF_3$, X is Cl and R is H. In this process the carboxylic acid anhydride is selected from the group consisting of acetic anhydride, propionic anhydride, butyric anhydride, succinic anhydride, glutaric anhydride, adipic anhydride, and formic anhydride. The reactive metal powder is as described above. In some embodiments of this process, the reductive dehydroxyhalogenation can be done without neutralizing the product mixture from the reaction of a halofluorocarbon with a reactive metal and an aldehyde. In other embodiments, the reductive dehydroxyhalogenation is done after first isolating the hydrofluoroalkanol, and then reacting it with a carboxylic acid anhydride and a reactive metal. In some embodiments, the reductive dehydroxyhalogenation is done without isolating the ester. In other embodiments, the reductive dehydroxyhalogenation is done with the ester being isolated from the solvent and metal salts, and then reacted with the reactive metal.

In some embodiments, the product of the reductive dehydroxyhalogenation further comprises a substituted cyclobutane of the formula cyclo-(—CF($R_f$)CHRCF($R_f$)CHR—), wherein $R_f$ is a perfluoroalkyl group having from one to four carbon atoms and R is $CH_3$, $CH_3CH_2$, $CH_3CH_2CH_2$, $(CH_3)_2CH$ or H. In one particular embodiment, $R_f$ is $CF_3$ and R is H.

In one embodiment, the carboxylic acid anhydride is selected from the group consisting of acetic anhydride, propionic anhydride, butyric anhydride, succinic anhydride, glutaric anhydride, adipic anhydride, and formic anhydride. In another embodiment, the carboxylic acid anhydride is acetic anhydride. In one embodiment, the mole ratio of carboxylic acid anhydride to hydrofluoroalkanol is from about 1:1 to about 2:1. In another embodiment, the mole ratio of carboxylic acid anhydride to hydrofluoroalkanol is from about 1.4:1 to about 1.8:1. In one embodiment, the mole ratio of reactive metal to hydrofluoroalkanol is about 1:1. In another embodiment, the mole ratio of reactive metal to hydrofluoroalkanol is about 2:1. In yet another embodiment, the mole ratio of reactive metal to hydrofluoroalkanol is about 2.5:1. The reaction between the metal hydrofluoroalkoxide and the carboxylic acid anhydride produces an ester of the formula $R_f$CFXCHROC(=O)R' where $R_f$ is as described above, R is as described above, X is as described above, and R' is the residue from the carboxylic acid anhydrides described above, and is selected from the group consisting of —$CH_3$, —$C_2H_5$, —$CH_2CH_2CH_3$, $CH_2CH_2CO_2H$, $CH_2CH_2CH_2CO_2H$, $CH_2CH_2CH_2CH_2CO_2H$, and H. In one embodiment, $R_f$ is $CF_3$, R is H, X is Cl, and R' is $CH_3$.

In one embodiment, the reductive dehydroxyhalogenation is conducted in a reaction solvent which is the same solvent in which the reaction of a halofluorocarbon with reactive metal and an aldehyde is conducted in. In another embodiment, the reductive dehydroxyhalogenation is conducted in a reaction solvent which is a different solvent than the reaction of a halofluorocarbon with reactive metal and an aldehyde is conducted in. In yet another embodiment, the reductive dehydroxyhalogenation is conducted in a mixture of pyridine or an alkyl-substituted pyridine, and dimethylformamide.

In one embodiment, the product of the esterification of the hydrofluoroalkanol is a compound having the formula: $R_f$CFXCHROC(=O)R' where $R_f$ is a perfluoroalkyl group having from one to four carbon atoms, R is $CH_3$, $CH_3CH_2$, $CH_3CH_2CH_2$, $(CH_3)_2CH$ or H, X is selected from Cl, Br, and I, and R' is selected from the group consisting of —$CH_3$, —$C_2H_5$, —$CH_2CH_2CH_3$, $CH_2CH_2CO_2H$, $CH_2CH_2CH_2CO_2H$, $CH_2CH_2CH_2CH_2CO_2H$ and H.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the preparation of 2-chloro-3,3,3-trifluoropropanol from 1,1,1-tetrafluoro-2,2-dichloroethane.

A 400 ml Hastelloy C shaker tube was charged with 32.8 g (0.5 mol) of activated Zinc powder, 12 g (0.5 mol) of paraformaldehyde and 180 ml anhydrous DMF under $N_2$. The tube was cooled down to −15° C. and 64.4 g (0.2 mol) of 1,1-dichlorotetrafluoroethane were added. Then the reaction mixture was stirred at 50° C. for 6 hours. The results of gas chromatography analysis of the reaction are summarized in Table 1. After the reaction mixture cooled down to room temperature, it was poured into a 200 ml mixture of ice, 10% aqueous HCl and 200 ml diethyl ether with stirring. After another 30 min stirring, the organic layer was separated and washed with 100 mL of 2% aqueous HCl and then 100 mL brine. After it was dried with $MgSO_4$, diethyl either was removed by vacuum to afford 13.36 of product (yield 8%).

TABLE 1

| Component | GC area percent (%) |
|---|---|
| 2-chloro-2,3,3,3-tetrafluoropropanol | 7.076 |
| 2-chloro-1,1,1,2-tetrafluoroethane | 8.18 |
| Methanol | .335 |
| DMF | 83.9 |

Example 2

Example 2 demonstrates the conversion of 2-chloro-2,3,3,3-tetrafluoropropanol to 2,3,3,3-tetrafluoro1-propene.

A 400 ml Hastelloy C shaker tube was charged with 26 g (0.4 mol) of activated Zinc powder, 33.3 g (0.2 mol) of 2-chloro-2,3,3,3-tetrafluoropropanol, 30.6 g (0.3 mol) of acetic anhydride and 180 ml anhydrous DMF under $N_2$. Then the reaction mixture was stirred at 50° C. for 6 hours. After the reaction mixture cooled down to room temperature, the product was collected in a cold trap chilled by dry ice to produce 18.1 g of 2,3,3,3-tetrafluoropropene.

Example 3

Example 3 demonstrates the synthesis of 2,3,3,3-tetrafluoro-1-propene from 1,1,1,2-tetrafluoro-2,2-dichloroethane.

A 400 ml Hastelloy C shaker tube was charged with 20 g (0.315 mol) of activated Zinc powder, 7.5 g (0.25 mol) of paraformaldehyde and 130 ml anhydrous DMF under $N_2$. The tube was cooled down to −15° C. and 43 g (0.25 mol) of 1,1-dichlorotetrafluoroethane were added. Then the reaction mixture was stirred at 60° C. for 6 hours. After the reaction mixture cooled down to room temperature, 30 g (0.46 mol) of activated Zinc powder and 50 g (0.5 mol) of acetic anhydride were added into the reactor. The reaction mixture was stirred at 50° C. for 6 hr and then cooled down to room temp. The gas phase and the liquid phase were analyzed by GC-MS. Results are summarized in Table 2.

TABLE 2

| | GC area percent (%) |
|---|---|
| Component (liquid phase) | |
| 2,3,3,3-tetrafluoropropene | 5.50 |
| 2-chloro-1,1,1,2-tetrafluoroethane | 16.93 |
| 3,4,4,4-tetrafluoro-2-butanone | 3.7 |
| Acetyl fluoride | 4.57 |
| Methyl acetate | 4.72 |
| Acetic acid | 52.7 |
| Acetic anhydride | 4.88 |
| Component (gas phase) | |
| 2,3,3,3-tetrafluoropropene | 83.42 |
| Tetrafluoroethylene | 0.75 |
| 1,1-difluoroethylene | 0.28 |
| Trifluoroethylene | 1.69 |
| 2-chloro-1,1,1,2-tetrafluoroethane | 11.62 |

Example 4

Example 4 demonstrates the synthesis of 2-chloro-2,3,3,3-tetrafluoropropanol ($CF_3CClFCH_2OH$) in pyridine.

A 80 ml Fisher Porter tube was charged with 2.24 g (0.034 mol) of activated Zinc powder, 1.24 g (0.041 mol) of paraformaldehyde and 30 ml anhydrous pyridine under $N_2$. The tube was cooled down to −15° C. and 5 g (0.029 mol) of 1,1-dichlorotetrafluoroethane were added. Then the reaction mixture was stirred at 50° C. for 8 hours. The pressure of the reactor dropped to 8 psig at end of reaction from 25 psig. After the reaction mixture was cooled down to room temperature, it was analyzed by GC-MS. For GC-MS analysis, a portion of the reaction mixture was acidified with a 10% solution of HCl in acetone. The data is reported by area percent of GC-MS in table 3.

TABLE 3

| Component | GC-MS area percent (%) |
|---|---|
| 2-chloro-2,3,3,3-tetrafluoropropanol | 8.586 |
| 2-chloro-1,1,1,2-tetrafluoroethane | 2.887 |

TABLE 3-continued

| Component | GC-MS area percent (%) |
|---|---|
| Methyl formate | 0.420 |
| Chlorotrifluoroethylene | 0.637 |
| Trifluoroethylene | .0140 |
| Methanol | 0.135 |
| Pyridine | 87.194 |

Example 5

Example 5 demonstrates the synthesis of 2-chloro-2,3,3,3-tetrafluoropropanol $CF_3CClFCH_2OH$ in dimethylacetamide.

A 80 ml Fisher Porter tube was charged with 2.23 g (0.034 mol) of activated Zinc powder, 1.21 g (0.040 mol) of paraformaldehyde and 30 ml anhydrous dimethylacetamide under $N_2$. The tube was cooled down to −15° C. and 5.2 g (0.030 mol) of 1,1-dichlorotetrafluoroethane were added. Then the reaction mixture was stirred at 60° C. for 4.5 hours. The pressure of the reactor dropped to 9 psig at end of reaction from 30 psig. After the reaction mixture was cooled down to room temperature, it was analyzed by GC-MS. For GC-MS analysis, a portion of the reaction mixture was acidified with a 10% solution of HCl in acetone. The data is reported by area percent of GC-MS in table 4.

TABLE 4

| Component | GC-MS area percent (%) |
|---|---|
| 2-chloro-2,3,3,3-tetrafluoropropanol | 5.750 |
| 2-chloro-1,1,1,2-tetrafluoroethane | 2.181 |
| Methyl formate | 0.181 |
| Chlorotrifluoroethylene | 2.634 |
| Trifluoroethylene | 0.029 |
| Dimethylacetamide | 88.463 |

Example 6

Example 6 demonstrates the synthesis of 2-chloro-2,3,3,3-tetrafluoropropanol $CF_3CClFCH_2OH$ in pyridine, with pretreatment of formaldehyde.

A 80 ml Fisher Porter tube was charged with 1.82 g (0.06 mol) of paraformaldehyde and 30 ml anhydrous pyridine under $N_2$. The tube was heated up to 60° C. and stirred at 60° C. for 4 hr. Then it was cooled down to room temp and 2.24 g (0.034 mol) of activated Zinc powder were added. After purging with $N_2$ for 15 min, the tube was cooled down to −15° C. and 5 g (0.029 mol) of 1,1-dichlorotetrafluoroethane were added. Then the reaction mixture was stirred at 50° C. for 8 hours. The pressure of the reactor dropped to 9 psig at end of reaction from 25 psig. After the reaction mixture was cooled down to room temperature, it was analyzed by GC-MS. For GC-MS analysis, a portion of the reaction mixture was acidified with a 10% solution of HCl in acetone. The data is reported by area percent of GC-MS in Table 5. The selectivity of 114a to $CF_3CClFCH_2OZnCl$ (analyzed as $CF_3CClFCH_2OH$) increased to 78.7%.

TABLE 5

| (Liquid phase) | |
|---|---|
| Component | GC-MS area percent (%) |
| 2,3,3,3-tetrafluoro-2-chloropropanol | 12.06 |
| 2-chloro-1,1,1,2-tetrafluoroethane | 3.07 |
| Methyl formate | 1.02 |
| Methanol | 0.102 |

TABLE 5-continued

| (Liquid phase) | |
| --- | --- |
| Component | GC-MS area percent (%) |
| Trifluoroethylene | 0.18 |
| pyridine | 83.55 |

Example 7

Example 7 illustrates the esterification of 2,3,3,3-tetrafluoro-2-chloropropanol with acetic anhydride to produce 2,3,3,3-tetrafluoro-2-chloropropyl acetate.

A 80 ml Fisher Porter tube was charged with 2 g (0.012 mol) of $CF_3CClFCH_2OH$ (which contains ~15% diethyl ether), 1.35 g (0.0132) of acetic anhydride and 0.25 g of concentrated sulfuric acid. The mixture was stirred at 60° C. for 6 hr. After the reaction mixture was cooled down to room temperature, it was analyzed by GC-MS. The data is reported by area percent of GC-MS in Table 6. This result shows that more than 99% of $CF_3CClFCH_2OH$ has been converted to $CF_3CClFCH_2OAc$.

TABLE 6

| Component | GC-MS area percent (%) |
| --- | --- |
| 2,3,3,3-tetrafluoro-2-chloropropyl acetate | 72.55 |
| 2,3,3,3-tetrafluoro-2-chloropropanol | 0.198 |
| Ethyl acetate | 3.12 |
| Acetic acid | 17.24 |
| Diethyl ether | 6.19 |

Example 8

Example 8 illustrates the direct esterification of $CF_3CClFCH_2OZnCl$ to $CF_3CClFCH_2OAc$.

10 ml of a pyridine solution containing about 14% $CF_3CClFCH_2OZnCl$ was vacuum evaporated at room temp to remove the majority of the pyridine. Then 2.0 g acetic anhydride and 1 ml DMF were added into the resultant solid. The mixture was stirred at 60° C. for 7 hr. After the reaction mixture was cooled down to room temperature, it was analyzed by GC-MS. The data is reported by area percent of GC-MS in Table 7.

TABLE 7

| Component | GC-MS area percent (%) |
| --- | --- |
| 2,3,3,3-tetrafluoro-2-chloropropyl acetate | 71.8 |
| 2,3,3,3-tetrafluoro-2-chloropropyl formate | 2.01 |
| 2,3,3,3-tetrafluoro-2-chloropropanol | 0.115 |
| Acetic anhydride | 2.61 |
| Acetic acid | 2.58 |
| DMF/pyridine (solvent) | 13.22 |

Example 9

Example 9 illustrates the conversion of $CF_3CClFCH_2OAc$ to 2,3,3,3-tetrafluoropropene.

The reaction mixture from example 8, above, was stirred with 1 g of $Na_2CO_3$ to remove the acid generated in esterification step. Then 3 mol of DMF and 1.3 g of Zn were added. The reaction was run in 80 ml Fisher Porter tube at 50° C. for 2 hr and 60° C. for another 2 hr with stirring. The pressure of the reactor increased from 0 psig to 13 psig. After the reaction mixture was cooled down to room temperature, it was analyzed by GC-MS. The data is reported by area percent of GC-MS in Table 8. $CF_3CClFCH_2OAc$ became non-detectable in the liquid phase of the reactor. This result shows that $CF_3CClFCH_2OAc$ has been quantitatively converted to 2,3,3,3-tetrafluoropropene under the conditions above.

TABLE 8

| | GC-MS area percent (%) |
| --- | --- |
| Component (vapor phase) | |
| 2,3,3,3-tetrafluoropropene | 94.48 |
| 2,3,3,3-tetrafluoro-2-chloropropanol | 0.115 |
| Acetic anhydride | 1.62 |
| Methyl acetate | 0.815 |
| DMF | 1.05 |
| Pyridine | 2.05 |
| (Liquid phase) | |
| 2,3,3,3-tetrafluoropropene | 1.61 |
| Acetic anhydride | 1.45 |
| Methyl acetate | 0.61 |
| DMF | 86.24 |
| Pyridine | 9.98 |

Example 10

Example 10 demonstrates the reaction of 1,1-dichlorotetrafluoroethane with paraformaldehyde in a mixed solvent of dimethylformamide and pyridine to produce $CF_3CClFCH_2OZnCl$.

A 80 ml Fisher Porter tube was charged with 2.2 g Zn (0.037 mol), 0.3 g Zinc acetate (0.0016 mol), 2 g (0.067 mol) of paraformaldehyde, 15 g of anhydrous pyridine and 15 g of dimethylformamide under $N_2$. After $N_2$ purge for 15 min, the tube was cooled down to −15° C. and 5 g (0.029 mol) of 1,1-dichlorotetrafluoroethane were added. Then the reaction mixture was stirred at 50° C. for 2 hours. The pressure of the reactor dropped to 5 psig at end of reaction from 25 psig. After the reaction mixture cooled down to room temperature, it was analyzed by GC-MS. For GC-MS analysis, a portion of the reaction mixture was acidified with a 10% solution of HCl in acetone. Solvents DMF and pyridine are excluded from integration. The data is reported by area percent of GC-MS. The selectivity of 114a to $CF_3CClFCH_2OZnCl$ (analyzed as $CF_3CClFCH_2OH$) is 83% based on GC-MS analysis.

TABLE 9

| (Liquid phase) | | | | | | | |
| --- | --- | --- | --- | --- | --- | --- | --- |
| Trifluoroethylene | Acetic acid | Methyl formate | Methyl acetate | 2-chloro-1,1,1,2-tetrafluoro ethane | 2,3,3,3-tetrafluoro-propene | 2,3,3,3-tetrafluoro-2-chloropropanol | 2,3,3,3-tetrafluoro-2-chloropropyl acetate |
| 0.18% | 3.1% | 0.24% | 0.68% | 5.18% | 4.61% | 80.1% | 3.744% |

Example 11

Example 11 illustrates esterification of $CF_3CClFCH_2OZnCl$ directly to $CF_3CClFCH_2OAc$ with acetic anhydride in a solvent mixture.

Excess Zn was filtrated off from the reaction mixture from example 10, then was charged into a 80 ml Fisher Porter tube. 4.4 g of acetic anhydride (0.043 mol) were also added into the reactor. The mixture was stirred at 60° C. for 6 hr. After the reaction mixture cooled down to room temperature, it was analyzed by GC-MS. The data is reported by area percent of GC-MS in Table 10. Solvents DMF, pyridine and acetic anhydride are excluded from integration. This result shows that more than 94% of $CF_3CClFCH_2OZnCl$ has been converted to $CF_3CClFCH_2OAc$ at condition above.

TABLE 10

| | | | | Liquid phase | | | |
|---|---|---|---|---|---|---|---|
| Trifluoroethylene | 2-chloro-1,1,1,2-tetrafluoro ethane | 3-chloro-3,4,4,4-trifluoro-2-butanone | Ethyl methyl ether | Methyl acetate | 2-chloro-2,3,3,3-tetrafluoropropyl acetate | unknows | |
| 0.477% | 5.97% | 2.57% | 0.83% | 0.92% | 85.3% | 2.46% | |

Example 12

Example 12 illustrates the synthesis of 2,3,3,3-tetrafluoro1-propene from 1,1,1,2-tetrafluoro-2,2-dichloroethane in 3:1 pyridine:DMF solvent.

A 80 ml Fisher Porter tube was charged with 2.1 g Zn (0.032), 0.3 g Zinc acetate (0.0016 mol), 2 g (0.067 mol) of paraformaldehyde, 30 g anhydrous pyridine under $N_2$. After purging with $N_2$ for 15 min, the tube was cooled down to −15° C. and 5 g (0.029 mol) of 1,1-dichlorotetrafluoroethane were added. Then the reaction mixture was stirred at 50° C. for 3 hours. The pressure of the reactor dropped to 5.5 psig at end of reaction from 25 psig. After the reaction mixture cooled down to room temperature, it was analyzed by GC-MS. For GC-MS analysis, a portion of the reaction mixture was acidified with a 10% solution of HCl in acetone. Solvent pyridine was excluded from integration. The data is reported in Table 11 by area percent of GC-MS. The selectivity of 1,1-dichlorotetrafluoroethane to $CF_3CClFCH_2OZnCl$ (analyzed as $CF_3CClFCH_2OH$) is 81% based on GC-MS analysis.

Then the excess Zn was filtrated off from the reaction mix and it was charged into a 80 ml Fisher Porter tube. 10 ml Anhydrous DMF and 3.5 g of acetic anhydride (0.034 mol) were also added into the reactor. The mixture was stirred at 60° C. for 4 hrs. After the reaction mixture cooled down to room temperature, it was analyzed by GC-MS. The data is reported in Table 12 by area percent of GC-MS. Solvents DMF and pyridine are excluded from integration. This result shows that more than 98% of $CF_3CClFCH_2OZnCl$ has been converted, and selectivity to $CF_3CClFCH_2OAc$ and $CF_3CFClCH_2OCH_2OAc$ are 89%.

10 ml of reaction mix above was left in an 80 ml Fisher Porter tube, activated Zinc powder (1 g, 0.015 mol) was also added. The reaction was run in 80 ml Fisher Porter tube at 60° C. for 4 hr with stirring. The pressure of the reactor increased from 6 psig to 15.5 psig. After the reaction mixture cooled down to room temperature, it was analyzed by GC-MS. The data is reported by area percent of GC-MS. The result of vapor phase was listed in Table 13 and the result of liquid phase was reported in Table 14 (solvent DMF and pyridine was excluded from integration). $CF_3CClFCH_2OAc$ became non-detectable in liquid phase of reactor. Analysis shows that selectivity to 2,3,3,3-tetrafluoro-1-propene is about 94%, and selectivity to 1,3-bis-trifluoromethyl-1,3-difluorocyclobutane ($C_6H_4F_8$) is about 5%.

TABLE 11

| Compounds | GC-MS area % |
|---|---|
| Trifluoroethylene | 1.93 |
| Trifluoroacetaldehyde | 1.05 |
| 2-Chloro-1,1,1,2-tetrafluoro ethane | 12.77 |
| 1,1-Dichloro-1,2,2,2-tetrafluoroethane | 0.378 |
| 2,3,3,3-tetrafluoro-2-chloropropanol | 74.68 |
| 2,3,3,3-tetrafluoro-2-chloropropyl acetate | 1.648 |
| Unknowns | 6.39 |

TABLE 12

| Compounds | GC-MS area % |
|---|---|
| Trifluoroethylene | 0.68 |
| 2,3,3,3-tetrafluoropropene | 0.04 |
| 2-Chloro-1,1,1,2-tetrafluoro ethane | 8.74 |
| 1,1-Dichloro-1,2,2,2-tetrafluoroethane | 1.03 |
| 3-chloro-3,4,4,4-tetrafluoro-2-butanone | 1.445 |
| 2,3,3,3-tetrafluoropropyl acetate | 0.31 |
| 2,3,3,3-tetrafluoro-2-chloropropanol | 1.67 |
| 2,3,3,3-tetrafluoro-2-chloropropyl acetate | 65.39 |
| Acetic anhydride | 3.33 |
| 2-chloro-2,3,3,3-tetrafluoropropoxy methyl acetate | 6.47 |
| Unknowns | 7.42 |

TABLE 13

| Compounds | GC-MS area % |
|---|---|
| Tetrafluoroethylene | 0.08 |
| Trifluoroethylene | 5.84 |
| 1,1,1-trifluoroethane | 0.02 |
| 2,3,3,3-tetrafluoropropene | 79.93 |
| Chlorotrifluoroethylene | 0.06 |
| 2-Chloro-1,1,1,2-tetrafluoro ethane | 9.10 |
| $C_6H_4F_8$ | 4.00 |
| 2,3,3,3-tetrafluoropropyl acetate | 0.1 |
| Unknowns | 0.85 |

Example 13

Example 13 illustrates the synthesis of 2,3,3,3-tetrafluoro-1-propene from 1,1,1,2-tetrafluoro-2,2-dichloroethane in 1:1 pyridine:DMF solvent.

A 80 ml Fisher Porter tube was charged with 2.1 g Zn (0.032), 0.3 g Zinc acetate (0.0016 mol), 2 g (0.067 mol) of paraformaldehyde, 0.2 g Bis(hydrogenated alkyl)dimethyl ammonium acetate and 30 g anhydrous pyridine under $N_2$. After purging with $N_2$ for 15 min, the tube was cooled down to −15° C. and 5 g (0.029 mol) of 1,1-dichlorotetrafluoroethane were added. Then the reaction mixture was stirred at 50° C. for 3 hours. The pressure of the reactor dropped to 5.5 psig at end of reaction from 23 psig. After the reaction mixture cooled down to room temperature, it was analyzed by GC-MS. For GC-MS analysis, a portion of the reaction mixture was acidified with a 10% solution of HCl in acetone. Solvents DMF and pyridine are excluded from integration. The data is reported in Table 15 by area percent of GC-MS. The selectivity of 114a to $CF_3CClFCH_2OZnCl$ (analyzed as $CF_3CClFCH_2OH$) is about 85% based on GC-MS analysis.

Then 10 ml reaction mix was filtrated and charged into an 80 ml Fisher Porter tube. 10 ml anhydrous DMF and 3.5 g of acetic anhydride (0.034 mol) were also added into the reactor. The mixture was stirred at 60° C. for 4 hrs. After the reaction mixture cooled down to room temperature, it was analyzed by GC-MS. The data is reported in Table 16 by area percent of GC-MS. Solvents DMF and pyridine are excluded from integration. This result shows that more than 98% of $CF_3CClFCH_2OZnCl$ has been converted, and selectivity to $CF_3CClFCH_2OAc$ and $CF_3CFClCH_2OCH_2OAc$ are about 95%.

The reaction mix above was treated with 2 g $Na_2CO_3$ in 80 ml Fisher Porter tube. After $Na_2CO_3$ was filtrated off, activated Zinc powder (1 g, 0.015 mol) was added. The reaction was run in an 80 ml Fisher Porter tube at 60° C. for 4 hr with stirring. The pressure of the reactor increased from 5 psig to 18 psig. After the reaction mixture cooled down to room temperature, it was analyzed by GC-MS. The data is reported by area percent of GC-MS. The result of vapor phase was listed in Table 17 and the result of liquid phase was reported in Table 18 (solvent DMF and pyridine was excluded from integration). More than 99% $CF_3CClFCH_2OAc$ and more than 95% $CF_3CFClCH_2OCH_2OAc$ have been converted. Analysis shows that selectivity to 1234yf is about 98%, and selectivity to 1,3-bis-trifluoromethyl-1,3-difluorocyclobutane ($C_6H_4F_8$) is about 0.1%.

TABLE 14

| Compounds | GC-MS area % |
|---|---|
| Trifluoroethylene | 1.06 |
| Trifluoroacetaldehyde | 0.09 |
| 2,3,3,3-tetrafluoropropene | 0.03 |
| 2-Chloro-1,1,1,2-tetrafluoro ethane | 8.33 |
| 1,1-Dichloro-1,2,2,2-tetrafluoroethane | 1.55 |
| 2,3,3,3-tetrafluoro-2-chloropropanol | 85.70 |
| 2,3,3,3-tetrafluoro-2-chloropropyl acetate | 0.285 |
| Unknowns | 0.656 |

TABLE 15

| Compounds | GC-MS area % |
|---|---|
| 2-Chloro-1,1,1,2-tetrafluoro ethane | 3.17 |
| 1,1-Dichloro-1,2,2,2-tetrafluoroethane | 0.62 |
| 3-chloro-3,4,4,4-tetrafluoro-2-butanone | 0.32 |
| 2,3,3,3-tetrafluoro-2-chloropropanol | 1.74 |
| 2,3,3,3-tetrafluoro-2-chloropropyl acetate | 68.00 |
| 2-chloro-2,3,3,3-tetrafluoropropoxy methyl acetate | 7.63 |
| Unknowns | 1.32 |

TABLE 16

| Compounds | GC-MS area % |
|---|---|
| Trifluoroethylene | 0.72 |
| 2,3,3,3-tetrafluoropropene | 97.46 |
| Chlorotrifluoroethylene | 0.06 |
| $C_6H_4F_8$ | 0.1 |
| Unknowns | 0.1 |

TABLE 17

| Compounds | GC-MS area % |
|---|---|
| Trifluoroethane | 0.03 |
| 2,3,3,3-tetrafluoropropene | 35.26 |
| 2-Chloro-1,1,1,2-tetrafluoro ethane | 5.89 |
| $C_6H_4F_8$ | 0.25 |
| 2,3,3,3-tetrafluoro-2-chloropropanol | 0.22 |
| 2,3,3-trifluoro-2-propen-1-ol acetate | 1.04 |
| 2,3,3,3-tetrafluoro-2-chloropropyl acetate | 0.7 |
| 2,3,3,3-tetrafluoropropyl acetate | 0.42 |
| 2-chloro-2,3,3,3-tetrafluoropropoxy methyl acetate | 2.27 |
| Unknowns | 7.49 |

Example 14

Example 14 illustrates the synthesis of 2,3,3,4,4,4-hexafluoro-1-butene from 1,1,1,2,2,3-hexafluoro-3,3-dichloropropane in 1:1 pyridine:DMF solvent.

A 80 ml Fisher Porter tube is charged with 2.1 g Zn (0.032), 0.3 g Zinc acetate (0.0016 mol), 2 g (0.067 mol) of paraformaldehyde, 0.2 g Bis(hydrogenated alkyl)dimethyl ammonium acetate and 30 g anhydrous pyridine under $N_2$. After purging with $N_2$ for 15 min, the tube is cooled down to −15° C. and 6.4 g (0.029 mol) of 1,1,1,2,2,3-hexafluoro-3,3-dichloropropane was added. Then the reaction mixture is stirred at 50° C. for 3 hours. The pressure of the reactor drops to 5.5 psig at end of reaction from 23 psig. After the reaction mixture cooled down to room temperature, it is analyzed by GC-MS. For GC-MS analysis, a portion of the reaction mixture is acidified with a 10% solution of HCl in acetone. Solvents DMF and pyridine are excluded from integration. The data is reported in Table 18 by area percent of GC-MS. The selectivity of 216cb to $CF_3CF_2CClFCH_2OZnCl$ (analyzed as $CF_3CF_2CClFCH_2OH$) is about 85% based on GC-MS analysis.

Then 10 ml reaction mix is filtrated and charged into an 80 ml Fisher Porter tube. 10 ml anhydrous DMF and 3.5 g of acetic anhydride (0.034 mol) are also added into the reactor. The mixture is stirred at 60° C. for 4 hrs. After the reaction mixture cooled down to room temperature, it is analyzed by GC-MS. The data is reported in Table 19 by area percent of GC-MS. Solvents DMF and pyridine are excluded from integration. This result shows that more than 98% of $CF_3CF_2CClFCH_2OZnCl$ is converted and selectivity to $CF_3CF_2CClFCH_2OAc$ and $CF_3CF_2CFClCH_2OCH_2OAc$ are about 95%.

The reaction mix above is then treated with 2 g $Na_2CO_3$ in an 80 ml Fisher Porter tube. After $Na_2CO_3$ is filtrated off, activated Zinc powder (1 g, 0.015 mol) is added. The reaction is run in an 80 ml Fisher Porter tube at 60° C. for 4 hr with stirring. The pressure of the reactor increases from 5 psig to 18 psig. After the reaction mixture is cooled down to room temperature, it is analyzed by GC-MS. The data is reported by area percent of GC-MS. The result of vapor phase is listed in Table 20 and the result of liquid phase is reported in Table 21

(solvent DMF and pyridine was excluded from integration). More than 99% $CF_3CF_2CClFCH_2OAc$ and more than 95% $CF_3CF_2CFClCH_2OCH_2OAc$ are converted. Analysis shows that selectivity to 2,3,3,4,4,4-hexafluoro-1-butene is about 98%, and selectivity to 1,3-bis-pentafluoroethyl-1,3-difluorocyclobutane ($C_8H_4F_{12}$) is about 0.1%.

TABLE 18

| Compounds | GC-MS area % |
|---|---|
| 1,2,3,3,3-pentafluoro-1-propene | 0.9 |
| 1,1,1,2,2,3-hexafluoro-3-chloropropane | 7.1 |
| 1,1,1,2,2,3-hexafluoro-3,3-dichloropropane | 1.5 |
| $CF_3CF_2CFClCH_2OH$ | 84 |
| $CF_3CF_2CFClCH_2OAc$ | 0.3 |
| Unknowns | 0.9 |

TABLE 19

| Compounds | GC-MS area % |
|---|---|
| 1,1,1,2,2,3-hexafluoro-3-chloropropane | 2.5 |
| $CF_3CF_2CFClCH_2OH$ | 1.2 |
| $CF_3CF_2CFClCH_2OAc$ | 73 |
| 2-chloro-2,3,3,4,4,4-hexafluorobutoxy methyl acetate | 5.2 |
| Unknowns | 17 |

TABLE 20

| Compounds | GC-MS area % |
|---|---|
| 1,2,3,3,3-pentafluoro-1-propene | 0.5 |
| 2,3,3,4,4,4-hexafluoro-1-butene | 96.5 |
| $C_8H_4F_{12}$ | 0.1 |
| Unknowns | 0.1 |

TABLE 21

| Compounds | GC-MS area % |
|---|---|
| 2,3,3,4,4,4-hexafluoro-1-butene | 35.26 |
| 3-chloro-1,1,2,2,3-hexafluoropropane | 6.3 |
| $C_8H_4F_{12}$ | 0.6 |
| 2,3,3,4,4,4-hexafluoro-2-chloropropanol | 0.8 |
| 2,3,4,4,4-pentafluoro-2-propen-1-ol acetate | 1.4 |
| $CF_3CF_2CFClCH_2OAc$ | 0.6 |
| 2-chloro-2,3,3,4,4,4-hexafluoropropoxy methyl acetate | 1.8 |
| Unknowns | 7.8 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for the manufacture of hydrofluoroalkenes of the structure $R_fCF$=CHR, comprising reacting a hydrofluoroalkanol of structure $R_fCFXCHROH$ or a hydrofluoroalkoxide of structure $R_fCFXCHROMX$, wherein M is a reactive metal in the +2 oxidation state, with a carboxylic acid anhydride and a reactive metal in a reaction solvent to form a hydrofluoroalkene, wherein $R_f$ is selected from the group consisting of perfluoromethyl, perfluoroethyl, perfluoro-n-propyl, perfluoro-i-propyl, perfluoeo-n-butyl and perfluoro-i-butyl, X is selected Cl, Br and I, and R is selected from the group consisting of H, $CH_3$, $C_2H_5$, n-$C_3H_7$, and i-$C_3H_7$.

2. The process of claim 1, further comprising the step of isolating said hydrofluoroalkene.

3. The process of claim 2 wherein $R_f$ is $CF_3$ and R is H.

4. The process of claim 1 wherein the carboxylic acid anhydride is selected from the group consisting of acetic anhydride, propionic anhydride, butyric anhydride, succinic anhydride, glutaric anhydride, adipic anhydride and formic anhydride.

5. The process of claim 1 wherein the reactive metal is selected from the group consisting of magnesium turnings, activated zinc powder, aluminum, and a powder of any of the following metals: magnesium, calcium, titanium, iron, cobalt, nickel, copper, zinc indium, and combinations thereof.

* * * * *